United States Patent [19]
Couri

[11] Patent Number: 4,523,586
[45] Date of Patent: Jun. 18, 1985

[54] PROTECTIVE COVER FOR A LIMB OR A CAST

[75] Inventor: Mark S. Couri, East Peoria, Ill.

[73] Assignee: Sundstrand Corporation, Rockford, Ill.

[21] Appl. No.: 560,855

[22] Filed: Dec. 12, 1983

[51] Int. Cl.³ .............................................. A61F 13/00
[52] U.S. Cl. ...................................................... 128/82
[58] Field of Search ................. 128/82, DIG. 15, 157, 128/165; 2/67

[56] References Cited

U.S. PATENT DOCUMENTS

| | | | |
|---|---|---|---|
| 2,176,463 | 10/1939 | Meendsen | 128/82 X |
| 2,229,575 | 1/1941 | Kaplan | 128/82 X |
| 3,710,790 | 1/1973 | Lemon | 128/165 |
| 4,178,924 | 12/1979 | Baxter | 128/82 |
| 4,224,935 | 9/1980 | Metelnick | 128/82 |
| 4,363,317 | 12/1982 | Broucek | 128/82 |

Primary Examiner—John D. Yasko
Attorney, Agent, or Firm—Wood, Dalton, Phillips, Mason & Rowe

[57] ABSTRACT

A protective cover for a limb, cast or the like including a bag of flexible material substantially impervious to an element to be protected against. The bag includes an opening through which the limb or cast to be protected may be inserted and on the interior of the bag, adjacent the opening, is provided with mating fasteners so that the internal sides of the bag may be fastened together to conform the size and shape of the opening of the bag to the size and shape of the limb or cast on which it is worn. The exterior of the bag opposite the internal side mentioned above define a flap which in turn carries a first fastening device. A second fastener is disposed on the bag remotely from the first fastener and may be engaged by the first fasteners to hold the flap against the body of the bag.

9 Claims, 13 Drawing Figures

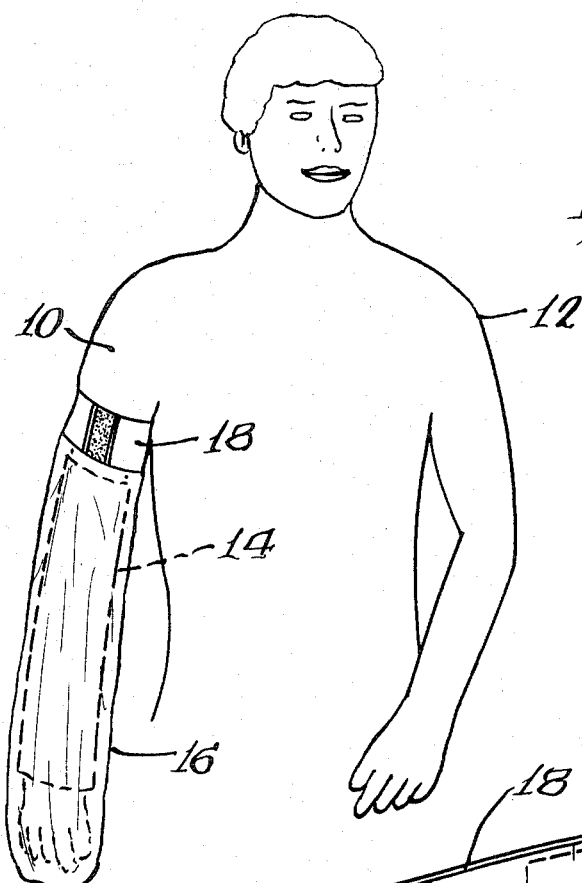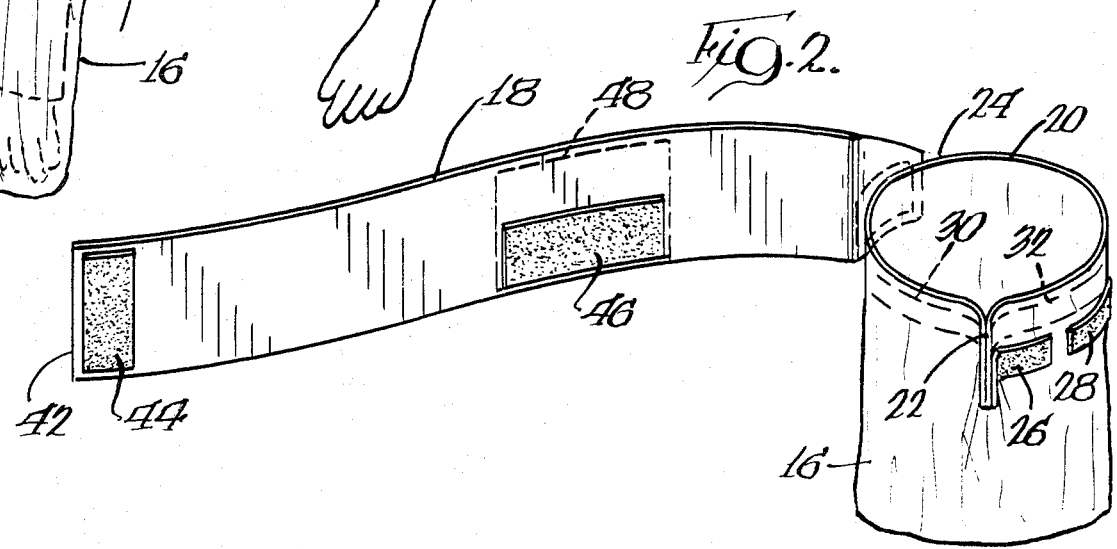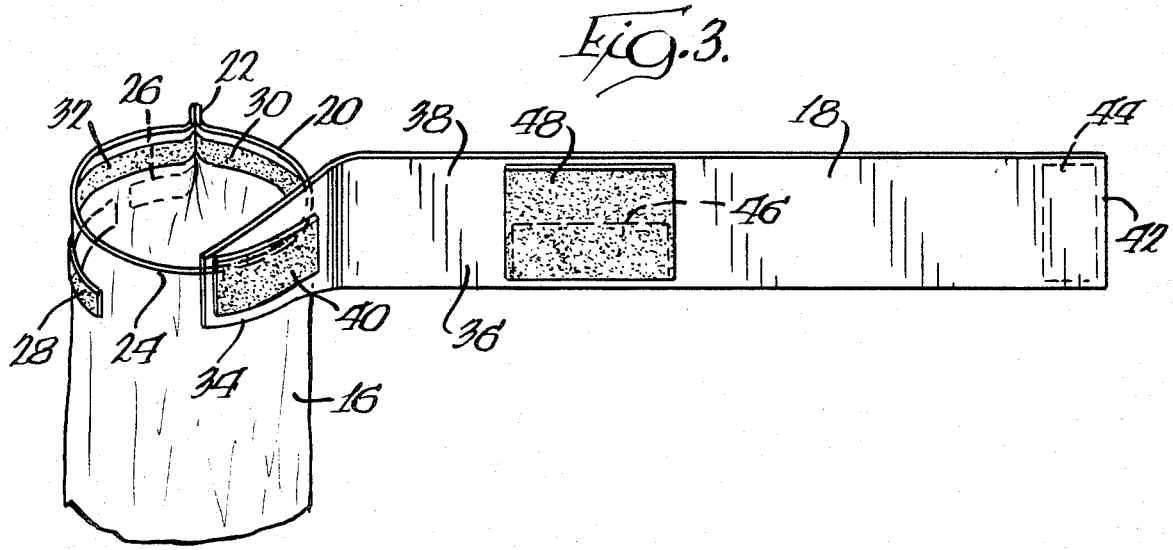

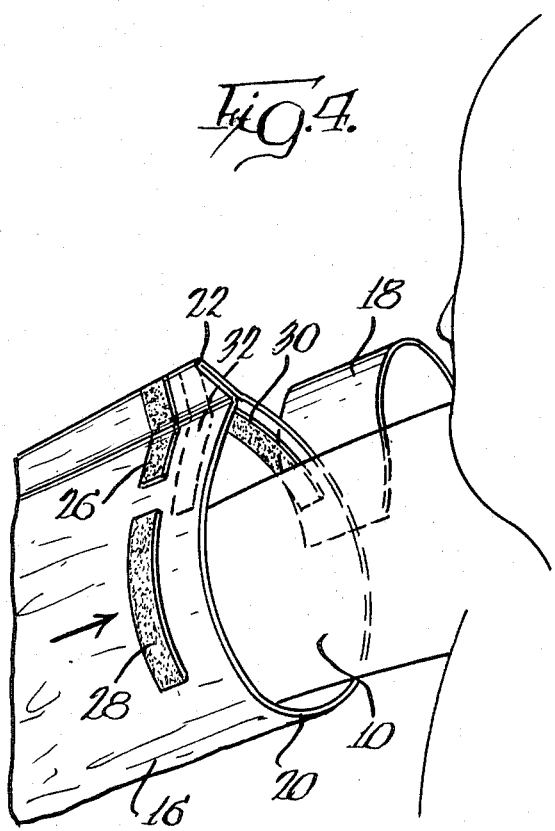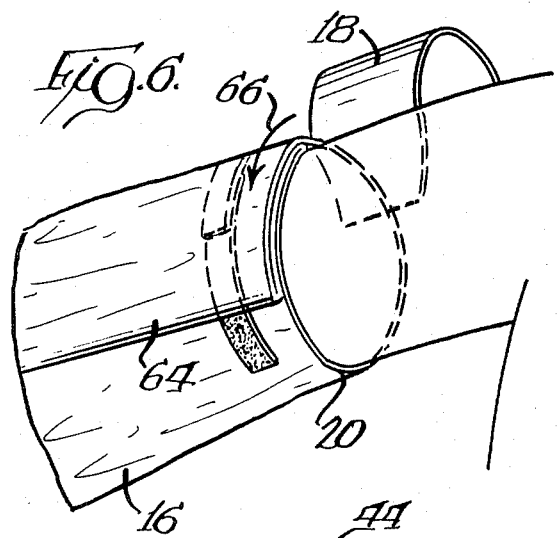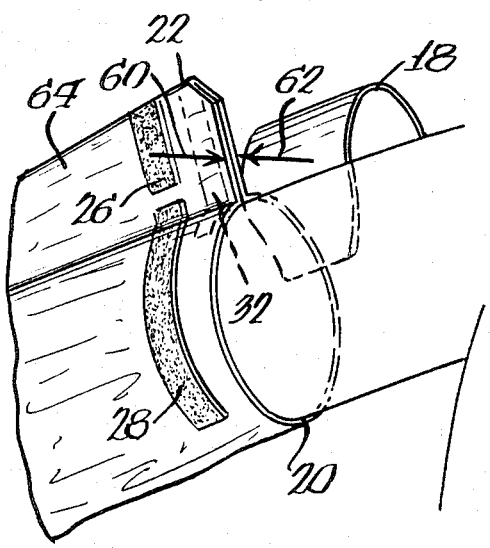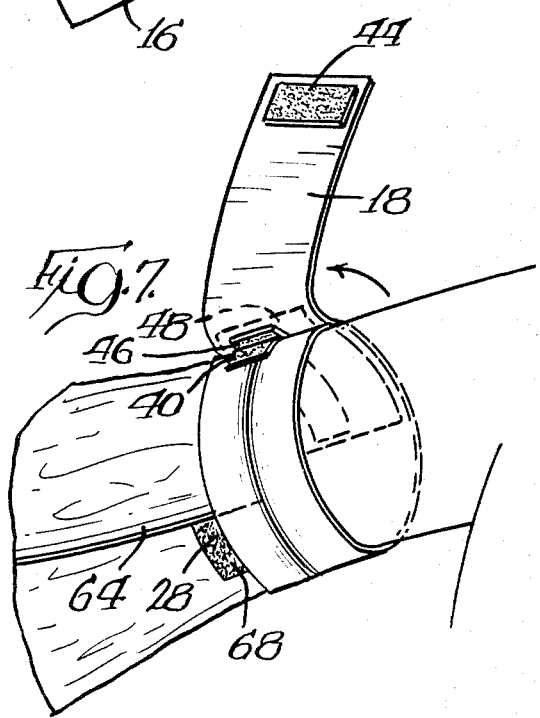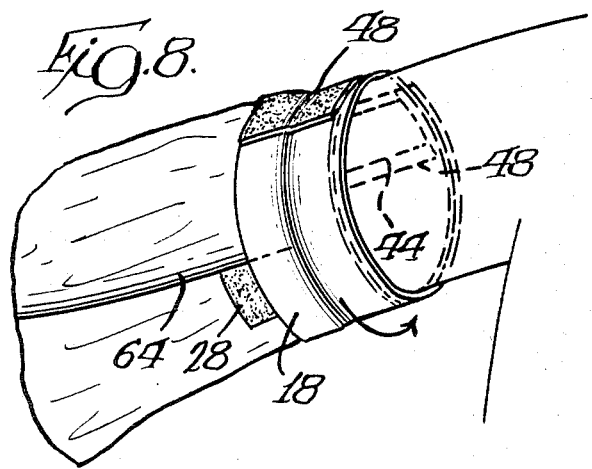

U.S. Patent  Jun. 18, 1985  Sheet 3 of 3  4,523,586
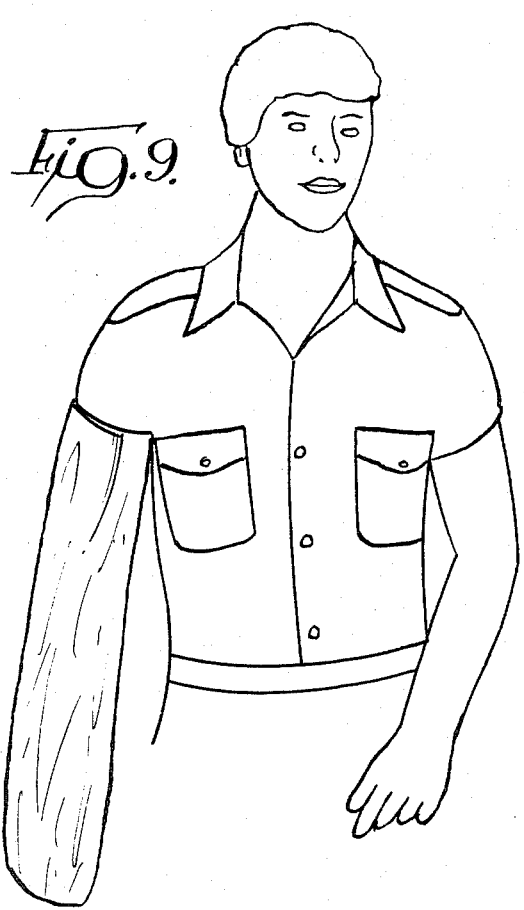
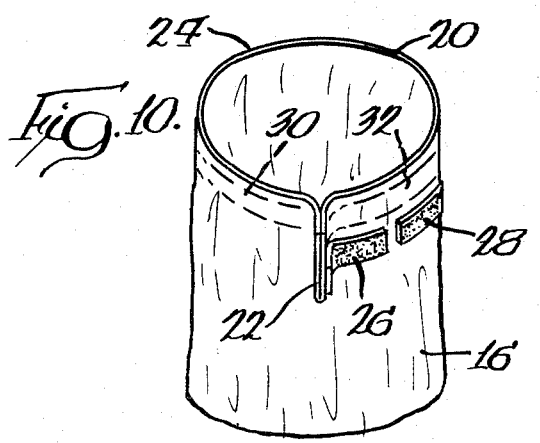
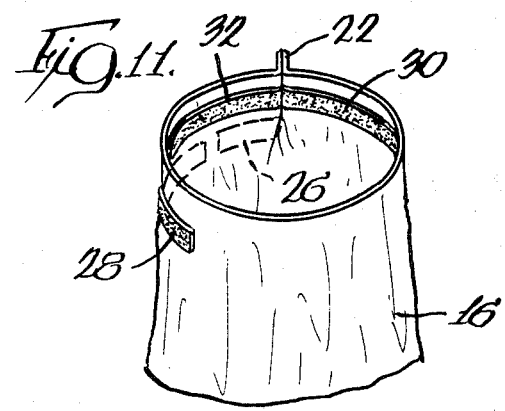
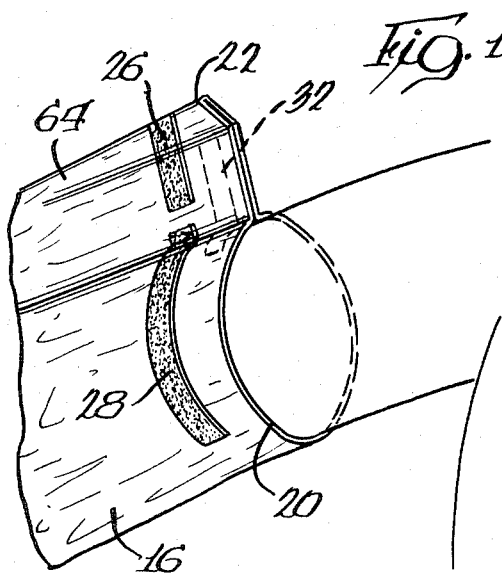
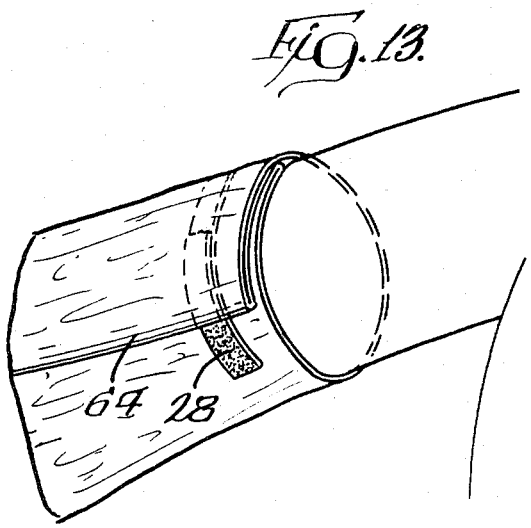

PROTECTIVE COVER FOR A LIMB OR A CAST

FIELD OF THE INVENTION

This invention relates to a protective cover for a limb such as a human arm or leg, or a cast on such a limb.

BACKGROUND ART

Over the years, many proposals have been developed for protective covers for limbs or casts. In some cases, the cover is to protect an article worn on the limb as, for example, a shoe, from the elements. Of course, cast protection is for the same purpose.

Other proposals have been specifically directed at the protection of casts so as to enable the wearer of the cast to shower or bathe without damaging the cast.

Prior art patents representative of the proposals are as follows. U.S. Pat. No. 2,176,463 to Meendsen issued Oct. 17, 1939; U.S. Pat. No. 2,229,575 to Kaplan issued Jan. 21, 1941; U.S. Pat. No. 3,710,790 to Lemon issued Jan. 16, 1973; U.S. Pat. No. 3,741,203 to Liman issued June 26, 1973; U.S. Pat. No. 3,747,125 to Goldman et al issued July 24, 1973; U.S. Pat. No. 3,804,084 to Lehman issued April 16, 1974; U.S. Pat. No. 3,845,769 to Shaw issued Nov. 5, 1974; U.S. Pat. No. 4,036,220 to Belasalma issued July 19, 1977; U.S. Pat. No. 4,078,266 to Brown issued Mar. 14, 1978; U.S. Pat. No. 4,224,935 to Metelnick issued Sept. 30, 1980; U.S. Pat. No. 4,330,887 to White issued May 25, 1982; and U.S. Pat. No. 4,363,317 to Broucek issued Dec. 14, 1982.

Of the foregoing, Broucek, Lemon, Meendsen and Kaplan may be of most relevance to the invention hereinafter described.

These proposals suffer from one or more deficiencies. For example, in the case of Broucek, while the protective cover is effective for its intended purpose, some difficulty may be experienced in fastening the elastic band necessary to seal the opening to the protective cover about the limb to be protected. Specifically, when the elastic band is stretched to assure a snug fit, the resulting tensile forces are applied through the length of the band to the cover at its opening and such force has a tendency to cause the cover to rotate on the limb of the user. Such rotation, of course, reduces the tension in the band which in turn reduces the length of the band such that the same cannot completely extend about the opening to seal the same. As a result, the user of the device restretches the band and the same result obtains. Thus, considerable frustration may be encountered in properly sealing the protective cover disclosed by Broucek.

Furthermore, the Broucek device cannot be used for extended periods of time. The necessary stretching of the elastic band applies a constrictive force about the limb of the user thereby impeding blood flow with the consequential effect of numbness in the limb or worse. If one attempts to utilize the Broucek device for protective functions over a period of time without stretching the band, the same is prone to slip and eventually fall off of the limb of the user.

The device disclosed by Kaplan is generally subject to the first mentioned deficiency of Broucek although the latter is somewhat eliminated in that Kaplan utilizes a drawstring for tightening the protective cover in addition to the elastic sealing strap such that the latter may be dispensed with when the cover is to be worn for an extended period of time. However, the Kaplan device utilizing the drawstring is not suitable for use on all limbs and is mainly intended for use with legs. When attempted to be applied to an arm, the drawstring cannot be easily manipulated by the user with a single free hand thereby requiring the presence of another person to tighten the drawstring.

Meendsen discloses a protective device which cannot be adequately sealed for cast protection purposes but is useful in some instances for the protection of shoes, exposed limbs, etc. from the elements.

Lemon discloses an elastic bandage which cannot be effectively sealed and generally should be regarded as of little relevance to the invention herein disclosed for that reason. It too is susceptible to twisting on the limb of the user during application.

The present invention is directed to overcoming one or more of the above problems.

SUMMARY OF THE INVENTION

It is the principal object of the invention to provide a new and improved protective cover for a limb or a cast. According to one embodiment of the invention, there is provided a protective cover that may be used for extended periods and which is easily applied to the limb of a user, whether an arm or a leg.

According to another facet of the invention, the protective cover may be completely sealed so as to allow its use as a protective cover during showers or the like.

The invention achieves the foregoing objects in an embodiment including a bag of flexible material substantially impervious to an element to be protected against. The bag has an opening through which the limb or cast to be protected may be inserted into the bag. The interior of the bag, adjacent the opening, is provided with a series of mating fasteners for fastening the internal sides of the bag together to thereby decrease the effective size of the opening to cause the size and shape of the opening to conform snugly to the size and shape of a limb or cast at its point of entry into the bag. The exterior of the bag opposite the internal sides, when the internal sides are fastened together, defines a flap. A first flap fastener is carried by the flap on the exterior of the bag adjacent the opening and a second flap fastener engageable with the first flap fastener is carried by the bag on its exterior adjacent the opening and remote from the flap. As a consequence, the opening may be substantially sealed about a limb or a cast by engaging the mating fasteners on the interior of the bag and thereafter folding the resulting flap about the bag to engage the first and second flap fasteners to secure the flap.

In a highly preferred embodiment, the fasteners employed are interference type fasteners of the type frequently sold under the registered trademark Velcro.

In one embodiment of the invention, there is provided a liquid impervious elastic band which has an end secured to the bag on the exterior thereof adjacent the opening in non-interfering relation with the first and second flap fasteners. The band is of sufficient length and elasticity so as to extend more than completely around the opening when the first and second flap fasteners are engaged and additional fastening means are provided for securing the band about the opening to seal the same. This embodiment of the invention is suitable for protection against water as, for example, when taking a shower. Preferably, the additional fastening means on the band cooperate with at least a portion of the second flap fastener to hold the bands securely in place about the opening.

Other objects and advantages will become apparent from the following specification taken in connection with the accompanying drawings.

DESCRIPTION OF THE DRAWINGS

FIG. 1 is a perspective view of one embodiment of a protective cover, including a sealing band, made according to the invention applied to the arm of a user;

FIG. 2 is a fragmentary perspective view of the protective cover;

FIG. 3 is a fragmentary perspective view of the protective cover taken oppositely of the view of FIG. 1;

FIG. 4 is a view showing a first stage of the application of a protective cover to the arm of a wearer;

FIG. 5 is a view similar to FIG. 4 showing a subsequent stage in the application of the cover;

FIG. 6 is a similar view showing still a subsequent stage in the application of the cover;

FIG. 7 is a similar view showing still a later stage in the application of the cover;

FIG. 8 is a similar view showing the cover as finally applied;

FIG. 9 is a view of another embodiment of the protective cover made according to the invention applied to the arm of a user;

FIG. 10 is a fragmentary perspective view of the modified embodiment;

FIG. 11 is a fragmentary perspective view of the modified embodiment taken oppositely of the view of FIG. 10;

FIG. 12 is a view illustrating a first step in the application of the modified embodiment to the arm of a wearer; and FIG. 13 illustrates the final step in the application of the modified embodiment.

DESCRIPTION OF THE PREFERRED EMBODIMENTS

An exemplary embodiment of a protective cover made according to the invention is illustrated on the arm 10 of a user 12. However, it should be appreciated that the use of the protective cover is not limited to arms, but may be used on legs as well.

As seen in dotted lines, the arm 10 is in a cast 14, which cast is surrounded by a bag 16. The bag is made of flexible material and typically will be open only at its upper end. The flexible material most usually will be liquid impervious but in some cases, depending upon the type of protection desired, need only be impervious to the element to be protected against. For example, where absolute protection against a liquid is not an essential characteristic of the cover, the same could be made of a tight weave fabric to provide protection against the wind or the like. In any event, the particular material of which the bag 16 is made is dependent upon its ultimate intended use and forms no part of the present invention.

As noted previously, the bag 16 has an open upper end and as seen in FIG. 1, such end is sealed by an elastic band 18 typically formed of moisture impervious material which is stretched about and sealed against the arm 10 of the user 12. In some instances, the sealing just described will take place against the upper end of the cast 14 but generally, the sealing will be against the arm 10, either against the flesh thereof or against a garment being worn on the arm.

Turning now to FIGS. 2 and 3, the upper opening of the bag 16 is illustrated at 20 and the same may be described as generally teardrop-shaped in that the same has an apex 22 and a generally circular section 24. The apex 22 may be formed simply by gathering a small amount of the material forming the bag 16 and stitching the same together.

As best seen in FIG. 2, the exterior of the bag 16, to one side of the apex 22, is provided with a small strip of fastening material 26. Spaced somewhat therefrom in alignment with respect thereto and in adjacency to the opening 20 is an elongated strip of mating fastening material 28. Preferably, the fastening material 26 and 28 will be of the interference type fastener such as is commonly marketed under the registered trademark Velcro. However, other fasteners, including snap fasteners may be used. It is preferred to use interference fasteners of the Velcro-type since the same provide for an infinite number of interengaging positions of the fasteners to thereby accommodate limbs of vastly varying circumferences.

On the interior of the bag, as best seen in FIG. 3, to each side of apex 22 are elongated strips 30 and 32 of interference-type fastening material. The strips 30 and 32 are chosen so that they mate with each other and are disposed in close proximity to the opening 20.

The elastic band 18 has one end 34 secured as by stitching (not shown) to the bag 16 at a location on the circular section 24 thereof spaced from the strips 26 and 28 so as to be in non-interfering relation therewith. The disposition of the band 18 is such that a lower part 36 thereof overlies the upper edge of the bag 16 while an upper part 38 of the band 18 extends above the opening 20. The length of the band 18 and the elasticity thereof are chosen such that the band 18 may be stretched more than completely about the opening 20 when the same has been snugly brought into engagement with the limb of a user or a cast. With this characteristic, the band may be stretched completely about the opening 20 and because of the fact that it is stretched, will exert a constricting pressure on both the upper end of the bag 16 and on the arm 10 of the user to effect a seal of the interior of the bag from the exterior thereof.

To hold the band 18 in such a relationship, the same is provided with fastening means in the form of interference-type fasteners. Specifically, the outer side of the band 18 relative to the bag 18 is provided with such a fastener 40 at the end 34. The opposite end 42 of the band 18 is provided with a mating fastener 44 on the inner side of the band 18 relative to the bag 16.

Intermediate the ends of the band 18, both sides of the same are provided with strips of fastening material shown at 46 and 48. The strip 46 is located on the inner side of the band 18 relative to the bag and is chosen so as to mate or coact with the strip 28 and the strip 40 on the exterior of the band 18 at the end 34. The fastener strip 48 is chosen to coact with the strip fastener 44 on the end 42 of the band 18.

The placement of the protective cover on a limb, whether an arm or a leg, will be apparent from FIGS. 4-8. The limb, such as a right arm 10 is inserted through the opening 20 of the bag 16, generally with the apex 22 uppermost, as shown in FIG. 4. With the free hand, the user, beginning at the apex 22, engages the fasteners 30 and 32 by exerting a pinching force shown by arrows 60 and 62 in FIG. 5 until the size and shape of the opening 20 conforms to that of the arm or the upper end of the cast at the point at which such portion enters the opening 22. As a consequence, at the apex 22, a flap 64 is formed, such flap carrying the fastener 26. Adjacent the flap 64 will be the fastener 28 and as seen in FIG. 6, the flap 64 is folded over the engage the fasteners 26 and 28. This assures that the opening 20 will remain in snug conformance with the limb or the cast inserted therethrough.

The elastic band 18 is then grasped and rotated in the direction of an arrow 66 as shown in FIG. 6 while being stretched. Depending upon the circumference of the limb, and the degree of stretching force applied to the band 18, the fastener 46 will be brought into mating engagement with either the fastener 40 or some exposed portion 68 of the strip 28. Continued stretching and wrapping of the band 18 will bring the fastener 44 to the point where it may matingly engage the fastener 48 at which time the protective cover will have assumed the configuration illustrated in FIG. 8 wherein the opening 20 is completely sealed by the band 18.

For placement on a right leg, the procedure is the same while for placement on a left limb, the apex 22 is originally generally located downwardly or rearwardly.

It has been found that the steps of application illustrated in FIGS. 4-6 inclusive, by reason of the provision of the fasteners 30 and 32 on the interior of the bag 16 adjacent the opening 20 prevent rotation of the bag 16 on the limb during the stretching and application of the band 18 thereby enabling the application to be performed solely with the free hand of the user where the protective cover is being applied to an arm. Thus, this feature eliminates difficulties encountered by users of various prior art devices as mentioned previously.

Turning now to FIGS. 9-13, inclusive, another embodiment of the inventive protective cover is illustrated. This embodiment is identical to that just described with the exception that the band 18 and the fasteners 40, 44, 46 and 48 associated therewith are entirely omitted. Thus, like reference numerals for identical parts are shown. Application of the embodiment of FIGS. 9-13 is accomplished in the same fashion as that previously described except, of course, the steps of stretching an applying the band 18 are omitted in view of the lack of such band. The embodiment shown in FIGS. 9-13 is suitable for most protective purposes since the gross seal effected at the opening 20 through use of the fasteners 30 and 32 and the folding of the flap 64 and uniting of the fasteners 26 and 28 will generally be sufficiently liquid impervious to even provide some measure of protection during the taking of a shower.

In any event, the embodiment illustrated in FIGS. 9-13 is ideally suited for prolonged use since the constrictive force exerted against the limb of a user by an elastic band such as the band 18 is avoided. And the gross seal provided is sufficient for many purposes as, for example, protecting a limb or a cast during outdoor activity even where some precipitation may be occurring. It will also be appreciated that application of the embodiment illustrated in FIGS. 9-13 inclusive, is easily performed with the free hand of the user in the case of its application to an arm in that the interior fasteners 30 and 32, once united, maintain the configuration of the flap 64 so that it may be easily folded over to the position illustrated in FIG. 13 with a single hand.

I claim:

1. A protective cover for a limb, cast, or the like comprising:
   (a) a bag of flexible material substantially impervious to an element to be protected against, said bag having an opening through which the limb or cast to be protected may be inserted into the bag;
   (b) the interior of said bag, adjacent said opening, being provided with a series of mating fasteners for fastening the internal sides of said bag together to thereby decrease the effective size of said opening to cause the size and shape of the opening to conform snugly to the size and shape of a limb or cast at its point of entry into the bag;
   (c) the exterior of said bag opposite said internal sides, when said internal sides are fastened together defining a flap;
   (d) a first flap fastener carried by said flap on the exterior of said bag adjacent said opening; and
   (e) a second flap fasteners engageable with said first flap fastener carried by said bag on its exterior adjacent said opening and remote from said flap;
   (f) whereby said opening may be substantially sealed about a limb or a cast by engaging said mating fasteners and folding the resulting said flap about the bag to engage said first and second flap fasteners.

2. The protective cover of claim 1 wherein said fasteners are Velcro type fasteners.

3. The protective cover of claim 1 further including a liquid impervious flexible band having an end secured to said bag on the exterior thereof adjacent said opening in non-interfering relation with said first and second flap fasteners, said band being of sufficient length and flexibility as to extend more than completely around said opening when said first and second flap fasteners are engaged; and additional fastening means for securing said band about said opening to seal the same.

4. The protective cover of claim 3 wherein said second flap fastener and at least a portion of said additional fastening means are capable of fastening to each other to hold said band about said opening.

5. The protective cover of claim 1 wherein said fasteners are adjustable to vary the size of said flap and said opening to snugly fit limbs or casts of varying sizes.

6. A protective cover for a limb, cast, or the like comprising:
   (a) a bag of flexible material substantially impervious to an element to be protected against, said bag having a generally tear drop shaped opening having an apex and a generally round portion through which the limb or cast to be protected may be inserted into the bag;
   (b) the interior of said bag, adjacent said opening, being provided at each side of said apex with a series of mating fasteners for fastening the internal sides of said apex together to thereby decrease the effective size of said opening to cause the size and shape of the opening to conform snuggly to the size and shape of a limb or cast at its point of entry into the bag;
   (c) the exterior sides of said apex defining a flap when said internal sides are fastened together;
   (d) a first flap fastener carried by said flap on the exterior of said bag adjacent said opening; and
   (e) a second flap fasteners engageable with said first flap fastener carried by said generally round portion on the exterior of said bag adjacent said opening and remote from said flap;
   (f) whereby said opening may be substantially sealed about a limb or a cast by engaging said interior fasteners on said apex and folding the resulting said flap about the bag to engage said first and second flap fasteners.

7. The protective cover of claim 6 wherein fasteners are interference type fasteners and said interior apex side fastener and said second flap fastener comprise elongated strips.

8. The protective cover of claim 7 further including a liquid impervious flexible band having an end secured to said bag on the exterior thereof adjacent said opening in non-interfering relation with said first and second flap fasteners, said band being of sufficient length and flexibility as to extend more than completely around said opening when said first and second flap fasteners are engaged; and additional fastening means for securing said band about said opening to seal the same.

9. The protective cover of claim 8 wherein said additional fastening means comprise interference type fasteners on said band, there being one on each end thereof for coaction with each other and one intermediate the ends of said band on the inner side of said band for coaction with said second flap fasteners.

* * * * *

UNITED STATES PATENT AND TRADEMARK OFFICE
CERTIFICATE OF CORRECTION

PATENT NO. : 4,523,586
DATED : June 18, 1985
INVENTOR(S) : Mark S. Couri

It is certified that error appears in the above-identified patent and that said Letters Patent is hereby corrected as shown below:

On the title page, delete "[73] Assignee: Sundstrand Corporation, Rockford, Illinois".

Signed and Sealed this

Nineteenth Day of November 1985

[SEAL]

Attest:

DONALD J. QUIGG

Attesting Officer

Commissioner of Patents and Trademarks